United States Patent
Labuz et al.

(10) Patent No.: US 9,040,489 B2
(45) Date of Patent: May 26, 2015

(54) NANOCRYSTALLINE PHOTOCATALYTIC COLLOID, A METHOD OF PRODUCING IT AND ITS USE

(75) Inventors: Przemyslaw Labuz, Cracow (PL); Wojciech Macyk, Kryspinów (PL); Grazyna Stochel, Cracow (PL); Piotr B. Heczko, Cracow (PL); Magdalena Strus, Cracow (PL); Justyna Derdzinska, Cracow (PL)

(73) Assignee: Jagiellonian University, Krakow (PL)

( * ) Notice: Subject to any disclaimer, the term of this patent is extended or adjusted under 35 U.S.C. 154(b) by 178 days.

(21) Appl. No.: 13/148,192

(22) PCT Filed: Feb. 26, 2010

(86) PCT No.: PCT/PL2010/050007
§ 371 (c)(1),
(2), (4) Date: Nov. 8, 2011

(87) PCT Pub. No.: WO2010/098687
PCT Pub. Date: Sep. 2, 2010

(65) Prior Publication Data
US 2012/0071428 A1 Mar. 22, 2012

(30) Foreign Application Priority Data
Feb. 26, 2009 (PL) .................................. PL387353
Mar. 4, 2009 (PL) .................................. PL387404

(51) Int. Cl.
*B01J 21/06* (2006.01)
*A61L 2/18* (2006.01)
*B01J 35/00* (2006.01)
*A61L 12/08* (2006.01)
*B01J 37/00* (2006.01)
*C01G 23/047* (2006.01)
*C09C 1/36* (2006.01)
*C07F 7/28* (2006.01)

(52) U.S. Cl.
CPC ................ *B01J 35/004* (2013.01); *A61L 2/18* (2013.01); *A61L 12/088* (2013.01); *A61L 2202/24* (2013.01); *B01J 21/063* (2013.01); *B01J 35/0013* (2013.01); *B01J 35/006* (2013.01); *B01J 37/0072* (2013.01); *C01G 23/047* (2013.01); *C01P 2002/84* (2013.01); *C01P 2004/04* (2013.01); *C01P 2006/10* (2013.01); *C01P 2006/60* (2013.01); *C09C 1/3669* (2013.01)

(58) Field of Classification Search
CPC ....... A61L 2/18; A61L 12/088; B01J 37/0072; B01J 21/063
See application file for complete search history.

(56) References Cited

U.S. PATENT DOCUMENTS

2009/0005238 A1    1/2009   Falaras

OTHER PUBLICATIONS

Lee et al., Rapid Commun. Mass Spectrom., 2007, 21, p. 2023-2030.*
Dev et al., Fresen. Z. Anal. Chem., 1962, 190(3), p. 316-318.*
Chen et al., Chem. Rev., 2007, 107, p. 2891-2959.*
Ye et al., Langmuir, 2007, 23, p. 5630-5637.*
Lebrette et al., J. Eur. Ceram. Soc., 2006, 26, p. 2727-2734.*
Invitation to Pay Additional Fees and Partial International Search Report for PCT/PL2010/050007, mailed Jul. 19, 2011.
Written Opinion of the International Searching Authority for PCT/PL2010/050007, mailed Jul. 19, 2011.
International Preliminary Report on Patentability for PCT/PL2010/050007, issued Oct. 4, 2011.
Rajh et al., "Surface restructuring of nanoparticles: an efficient route for ligand-metal oxide crosstalk," *J. Phys. Chem. B* 106:10543-10552 (2002).
Tachikawa et al., "Probing the surface adsorption and photocatalytic degradation of catechols on $TiO_2$ by solid-state NMR spectroscopy," *Langmair* 22:893-896 (2006).
Rodriguez et al., "Surface complexation at the $TiO_2$ (anatase)/aqueous solution interface: chemisorption of catechol," *Journal of Colloid and Interface Science* 177:122-131 (1996).
de la Garza et al., "Surface states of titanium dioxide nanoparticles modified with enediol ligands," *J. Phys. Chem. B* 110:680-686 (2006).
Rajh et al., "Improving optical and charge separation properties of nanocrystalline $TiO_2$ by surface modification with vitamin C," *J. Phys. Chem. B* 103:3515-3519 (1999).

* cited by examiner

*Primary Examiner* — Jonathan S Lau
(74) *Attorney, Agent, or Firm* — Fish & Richardson P.C.

(57) ABSTRACT

The present invention relates to a nanocrystalline photocatalyst active upon visible light irradiation, with a high degree of dispersion, stable in the form of a transparent colloidal solution in an aqueous environment, containing nanocrystals of titanium dioxide ($TiO_2$) surface-modified via direct chemisorption of organic compounds. The present invention in turn relates to a method of producing the material as well as its use as a photosterilizer, photobacteriocide, photomycocide, and/or photocatalyst, in particular for the sterilization of glass surfaces, transparent plastics and transparent materials, in particular contact lenses, medical catheters, glass and plastic conduits as well as other surfaces, whose sterilization is desirable and/or required.

22 Claims, 4 Drawing Sheets

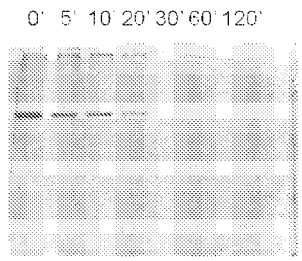
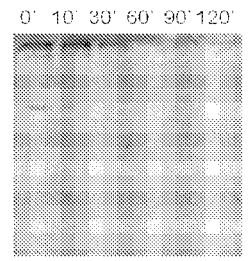
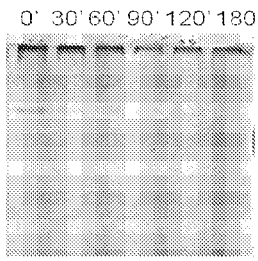
Fig. 3a    Fig. 3b    Fig. 3c
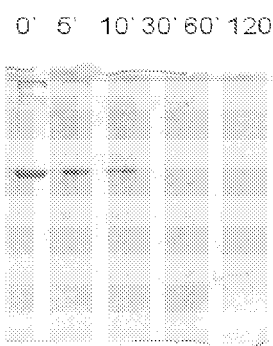
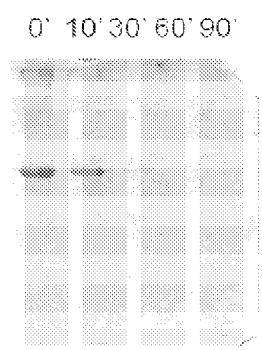
Fig. 3d    Fig. 3e
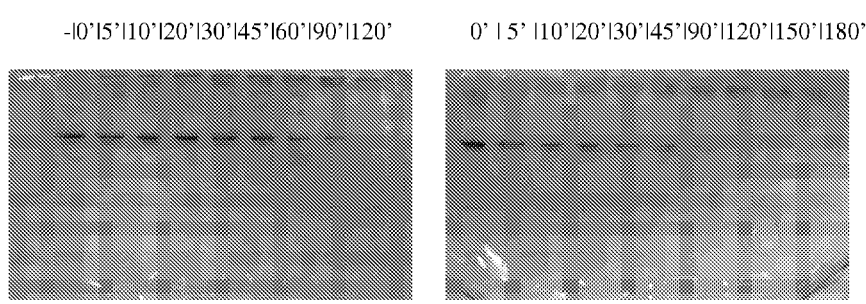
Fig. 3f    Fig. 3g

NANOCRYSTALLINE PHOTOCATALYTIC COLLOID, A METHOD OF PRODUCING IT AND ITS USE

CROSS REFERENCE TO RELATED APPLICATIONS

This application is a U.S. National Phase Application under 35 U.S.C. §371 of International Application PCT/PL2010/050007, filed on Feb. 26, 2010, which claims the benefit of Polish Application No. PL387353, filed on Feb. 26, 2009 and Polish Application No. PL387404, filed on Mar. 4, 2009, the entire contents of each of which are hereby incorporated by reference in their entireties.

TECHNICAL FIELD

The subject of the present invention is a nanocrystalline photocatalyst, active upon irradiation with visible light, in the form of a transparent colloidal solution, a method of producing transparent colloidal solutions of this material and its use.

The publication entitled "Surface restructuring of nanoparticles: an efficient route for ligand-metal oxide crosstalk" Rajh T. et al. (*J. Phys. Chem. B* 2002, 106, 10543-10552) discloses nanocrystals of titanium dioxide modified with endiol ligands, including ascorbic acid. Modification of metal oxide nanoparticles with ascorbic acid changed its physical and chemical properties. The chemical bonding of ascorbic acid to the surface of $TiO_2$ broadens the absorption spectrum of such a material to visible light. The colloid of $TiO_2$ modified with ascorbic acid is produced using a process carried out in aqueous solutions at low pH. Prior art does not reveal potential uses of this colloidal system.

BACKGROUND

The disadvantage observed in prior art is a system which works solely in an acidic environment, which greatly reduces the number of uses for such a colloidal solution.

The goal of the present invention is to deliver a transparent colloidal solution photoactive upon visible light irradiation, exhibiting strong photocatalytic and photosterilising properties. In a particular embodiment, it is desirable that it is also stable in a neutral aqueous environment (pH ca. 7). The goal of the present invention is also to deliver novel possibilities of using a colloidal solution of a nanocrystalline visible light active photocatalyst possessing a particular set of characteristics for the sterilization of various materials, such as those requiring the maintenance of physiological conditions such as contact lenses or medical catheters.

DETAILED DESCRIPTION

Unexpectedly, such a defined goal has been achieved by the present invention.

The goal of the present invention is a nanocrystalline photocatalyst photoactive upon visible light irradiation in the form of a transparent colloidal solution characterised in that it contains:

a) a dispersed phase containing nanoparticles of titanium dioxide $TiO_2$ of less than 100 nm in size modified on their surface with an organic compound selected from a group encompassing:
i. a compound described by the formula:

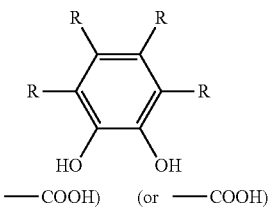

where R denotes —H, —$NH_2$, —$NH_3^+$ or —$SO_3M$, in which M denotes $H^+$, $K^+$, $Na^+$, $Li^+$, $NH_4^+$,
ii. ascorbic acid,
iii. a compound described by the formula:

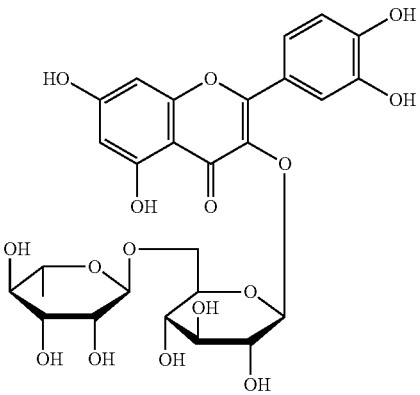

b) a dispersion medium, preferably an aqueous solution, preferably characterized by an approximately neutral pH.

Preferably, the nanocrystalline photocatalyst according to the present invention exhibits visible light absorption as well as photocatalytic activity in a wavelength range ($\lambda$) no smaller than ca. 400 nm (the arbitrary threshold between ultraviolet and visible light) to about 600 nm, preferably to ca. 700 nm, as well as absorption of ultraviolet light ($\lambda$<400 nm).

Equally preferably, it exhibits photocatalytic activity upon irradiation with visible light (wavelengths $\lambda$ higher than 400 nm).

Equally preferably, it exhibits photocatalytic activity upon irradiation with ultraviolet light (wavelengths $\lambda$ below 400 nm).

Preferably, the organic compound is a compound selected from the group encompassing: phthalic acid, 4-sulfophthalic acid, 4-amino-2-hydroxybenzoic acid, 3-hydroxy-2-naphthylic acid, salicylic acid, 6-hydroxysalicylic acid, 5-hydroxysalicylic acid, 5-sulfosalicylic acid, 3,5-dinitrosalicylic acid, disodium salt of 1,4-dihydroxy-1,3-benzenedisulfonic acid, gallic acid, pyrogallol, 2,3-naphthalenediol, 4-methylcatechol, 3,5-di-tert-butylcatechol, p-nitrocatechol, 3,4-dihydroxy-L-phenylalanine (DOPA), rutin as well as ascorbic acid.

Equally preferably, it exhibits stability in aqueous solutions at pH of about 7, and the compound bound to the surface (modifier) is a compound selected from the group encompassing: disodium salt of 4,5-dihydroxy-1,3-benzenedisulfonic acid, rutin and ascorbic acid.

Further modifications of nanoparticles dispersed in a colloidal solution according to the present invention are also possible, for example nanoparticles of titanium dioxide modified with an organic compound selected from the group defined above can be further bound with molecules which increase the specificity of its activity, preferably an antibody, peptide, biotin, or vitamins.

The next subject of the present invention is a method of producing nanocrystalline photocatalyst active in visible light in the form of a transparent colloidal solution, characterised in that a) a colloidal aqueous solution of $TiO_2$ is supplemented with an organic compound which undergoes chemisorption on the surface of $TiO_2$ selected from the group encompassing:
 i. a compound with the formula:

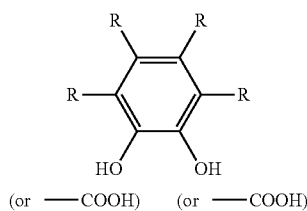

where R denotes —H, —$NH_2$, —$NH_3^+$ or —$SO_3M$, in which M denotes $H^+$, $K^+$, $Na^+$, $Li^+$, $NH_4^+$,
 ii. ascorbic acid,
 iii. a compound with the formula:

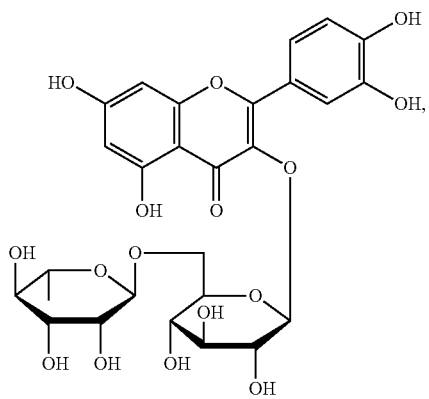

b) dialysis is performed on the resulting sol against an aqueous solution of i. and possibly it is apportioned for sale in the form of stable nanoparticle suspensions.

In a preferable embodiment of a method according to the present invention the sol produced in stage a) is brought to pH=7; with the exception of a method of producing the colloid described as variant 4B.

Preferably the organic compound is a compound selected from a group encompassing: phthalic acid, 4-sulfophthalic acid, 4-amino-2-hydroxybenzoic acid, 3-hydroxy-2-naphthylic acid, salicylic acid, 6-hydroxysalicylic acid, 5-hydroxysalicylic acid, 5-sulfosalicylic acid, 3,5-dinitrosalicylic acid, disodium salt of 1,4-dihydroxy-1,3-benzenedisulfonic acid, gallic acid, pyrogallol, 2,3-naphthalenediol, 4-methylcatechol, 3,5-di-tert-butylcatechol, p-nitrocatechol, 3,4-dihydroxy-L-phenylalanine (DOPA), rutin and ascorbic acid.

Preferably, the chemisorption is performed in an acidic environment, preferably at pH ca. 2.5, particularly in the presence of nitric acid. Equally preferably, following the chemisorption, the colloidal solution is brought to pH of about 7, preferably using an aqueous solution of a base and/or the chemisorption is performed in the presence of an alcohol, preferably isopropanol, whereas a colloidal solution of $TiO_2$ is supplemented with the organic compound at a molar ratio of 1:1.

The next subject of the present invention is the use of a nanocrystalline photocatalyst active in visible light in the form of a transparent colloidal solution according to the present invention, in making films (coatings), or in the production of a preparation for disinfection or sterilization, preferably in the manufacturing of a photosteriliser, a photobacteriocide, a photomycocide, a photocatalyst meant for use in one of the following areas: cosmetics, dermatology, ophthalmology, laryngology, urology, gynaecology, rheumatology, oncology, surgery, veterinary medicine, dentistry, in particular for the sterilization of glass or plastic elements, particularly contact lenses, medical catheters, glass and/or plastic conduits as well as other surfaces whose sterilization is preferable and/or required.

A material according to the present invention exhibits photocatalytic activity upon irradiation with visible light ($\lambda$>400 nm; photocatalysis is the result of the absorption of visible light by the titanium surface complex of the charge-transfer type) as well as ultraviolet light ($\lambda$<400 nm; photocatalysis is the result of the absorption of ultraviolet light by the titanium surface complex of the charge-transfer type or directly by the titanium dioxide). The irradiation generates so-called reactive oxygen species (OH., $O_2^-$, $H_2O_2$, $^1O_2$).

A nanocrystalline photocatalyst active in visible light in the form of a transparent colloidal solution according to the present invention as well as films (coatings) made using it are useful in medicine (for example in w dermatology, ophthalmology, laryngology, urology, gynaecology, rheumatology, oncology, surgery, veterinary medicine or dentistry) and cosmetics. A material according to the present invention is used in the production of products selected from a group encompassing: photosterilisers, photobacteriocides, photomycocides and photocatalysts. In particular, the present invention makes it possible to produce preparations for sterilising elements of glass and other materials, particularly transparent ones, for example contact lenses, medical catheters, and glass and plastic conduits.

BRIEF DESCRIPTION OF DRAWINGS

Example embodiments of the present invention have been shown in figures, in which

FIG. 3 shows the results of irradiation with visible light (using cut-off filters) of a reaction mixture (bovine albumin with a solution of colloidal $TiO_2$ nanocrystals modified respectively with compound K-1, ascorbic acid and rutin), in the electrophoretic image: K-1@$TiO_2$: (a) $\lambda$>400 nm, (b) $\lambda$>435 nm, (c) $\lambda$>455 nm, KA@$TiO_2$: (d) $\lambda$>400 nm, (e) $\lambda$>420 nm, rutin@$TiO_2$: (f) $\lambda$>420 nm, (g) $\lambda$>455 nm;

EXAMPLE 1

Figure 1A:
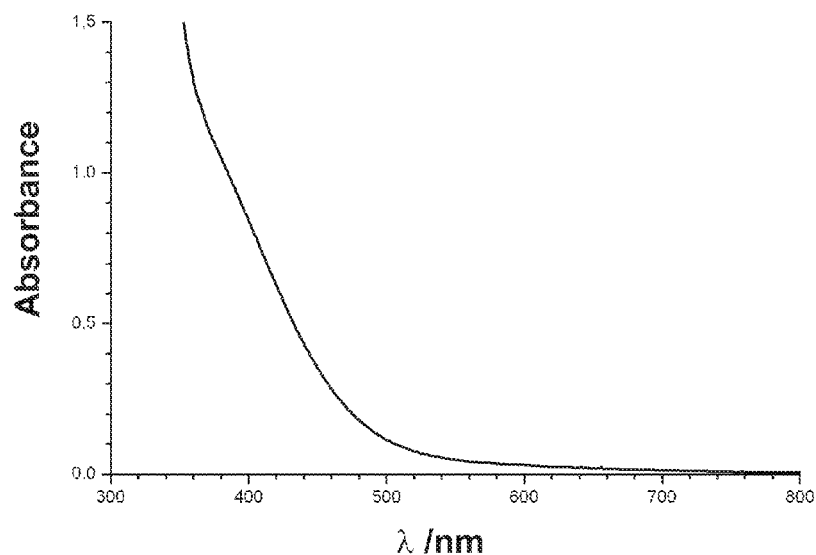
FIG. 1 shows UV-vis absorption spectra of a colloidal solution of $TiO_2$ nanocrystals modified respectively with compound K-1 (Table 2) (a), ascorbic acid (b) and rutin (c) (each concentration: 0.4 g/dm$^3$)

Production of a Nanocrystalline Photocatalyst Active in Visible Light

The initial substrate for the synthesis of the materials in question is an unmodified nanocrystalline $TiO_2$, which may be produced according to various known procedures. One of them is proposed by Wang et al. (*J. Phys. Chem. B,* 2000, 104, 93-104). Particles of titanium dioxide $TiO_2$ of less than 100 nm in size (estimated using imaging with a transmission electron microscope) is modified on its surface directly via chemisorption of an organic compound selected from the group according to the present invention with the formation of charge-transfer complexes. Photoinduced electron transfer occurs between the organic compound molecule and the semiconductor particle. A photoactive colloid according to the present invention is characterised by a high degree of dispersion and occurs in the form of a suspension or emulsion.

Variant 1.

A colloidal aqueous solution of $TiO_2$ (1.2 g/dm$^3$) containing isopropanol (10%) in a nitric acid ($HNO_3$) environment (pH=2.5) was supplemented with crystalline 4,5-dihydroxy-1,3-benzenedisulfonic acid disodium salt (K-1; Table 2) at a molar ratio of 1:1 (modifier:$TiO_2$). A yellow precipitate was formed. The resulting suspension was alkalised with an NaOH solution to pH=7 (causing the precipitate to dissolve). The solution was placed in a dialysis tube and dialysed twice against water or an appropriate buffer (i.e. SSC or PBS) in order to remove alcohol and the excess of modifier not bound with $TiO_2$. A yellow, clear colloidal solution was produced, which was used in further experiments.

The method described is equally suitable for synthesizing nanocrystalline $TiO_2$ modified with catechol derivatives or salicylic acid or phthalic acid derivatives (syntheses 2 and 3, Tables 1 and 2). In these cases it proved impossible to obtain stable materials (ones that do not undergo aggregation) at pH ≈7.

Variant 2.

A colloidal aqueous solution of $TiO_2$ (1.2 g/dm$^3$) containing isopropanol (10%) in a nitric acid environment (pH=2.5) was supplemented with a compound from the group A (A-1: A-2; phthalic acid derivatives) or S (S-1:S-7; salicylic acid derivatives; Table 1) in crystalline form, at a molar ratio of 1:1 (modifier:$TiO_2$). The colloidal solution changed its colour. The resulting colloidal solution was alkalised with an NaOH solution to pH=7. The solution was placed in a dialysis tube and dialysed twice against water, in order to remove alcohol and any modifier not bound with $TiO_2$.

TABLE 1

Phthalic acid and salicylic acid derivatives.

| Compound symbol | Compound name | Structural formula |
|---|---|---|
| A-1 | phthalic acid | (structure) |
| A-2 | 4-sulfophthalic acid | (structure) |
| S-1 | 4-amino-2-hydroxybenzoic acid | (structure) |
| S-2 | 3-hydroxy-2-naphthalic acid | (structure) |
| S-3 | salicylic acid | (structure) |
| S-4 | 6-hydroxysalicylic acid | (structure) |
| S-5 | 5-hydroxysalicylic acid | (structure) |
| S-6 | 5-sulfosalicylic acid | (structure) |
| S-7 | 3,5-dinitrosalicylic acid | (structure) |

Variant 3.

A colloidal aqueous solution of $TiO_2$ (1.2 g/dm$^3$) containing isopropanol (10%) in a nitric acid environment (pH=2.5) was supplemented with a compound from the group K (K-2: K-8; Table 2) at a molar ratio of 1:1 (modifier:$TiO_2$). The colloidal solution changed its colour. The resulting colloidal solution was alkalised with an NaOH solution to pH=7. The solution was placed in a dialysis tube and dialysed twice against water, in order to remove alcohol and any modifier not bound with $TiO_2$.

TABLE 2

Catechol derivatives.

| Compound symbol | Compound name | Structural formula |
|---|---|---|
| K-1 | disodium salt of 1,4-dihydroxy-1,3-benzenedisulfonic acid |  |
| K-2 | gallic acid |  |
| K-3 | pyrogallol |  |
| K-4 | 2,3-naphthalenediol |  |
| K-5 | 4-methylcatechol |  |
| K-6 | 3,5-di-tert-butylcatechol |  |
| K-7 | p-nitrocatechol |  |

TABLE 2-continued

Catechol derivatives.

| Compound symbol | Compound name | Structural formula |
|---|---|---|
| K-8 | 3,4-dihydroxy-L-phenylalanine (DOPA) | 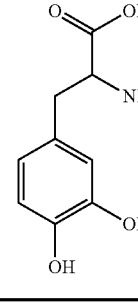 |

Variant 4A.

A colloidal aqueous solution of $TiO_2$ (1.2 g/dm$^3$) containing isopropanol (10%) in a nitric acid environment (pH=2.5) was supplemented with a compound with the formula (rutin):

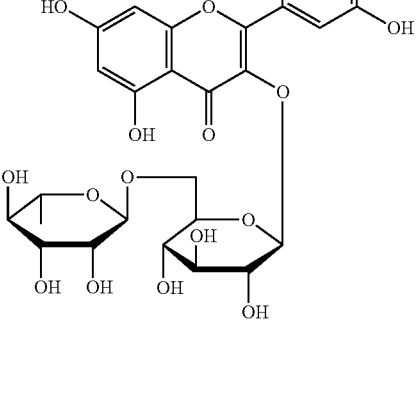

at a molar ratio of 1:1 (rutin:$TiO_2$). An orange precipitate was formed. The resulting suspension was alkalised with a NaOH solution to pH=9 (causing the precipitate to dissolve). The solution was placed in a dialysis tube and dialysed three times: The first dialysis was performed against an aqueous solution of NaOH, pH=9. The subsequent two dialyses were performed against distilled water, and appropriate buffer (i.e. SSC or PBS, pH≈7) in order to remove alcohol and any modifier not bound with $TiO_2$. An orange, clear colloidal solution was obtained which was used in subsequent experiments.

Variant 4B.

A colloidal aqueous solution of $TiO_2$ (1.2 g/dm$^3$) containing isopropanol (10%) in a nitric acid environment (pH=2.5) was supplemented with a crystalline compound with the formula (rutin):

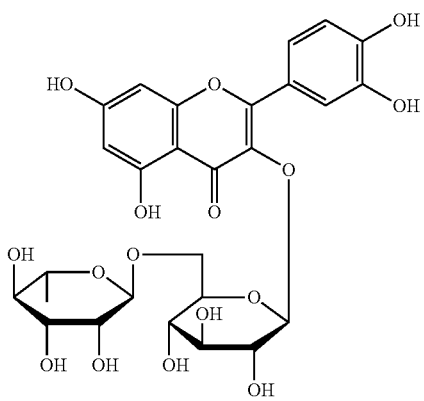

at a molar ratio of 1:1 (rutin:TiO$_2$). An orange precipitate appeared. The resulting suspension was centrifuged. The precipitate was rinsed several times with an aqueous HCl solution (pH 2 to 4) until excess modifier (rutin) was rinsed out, which was confirmed spectrophotometrically. Next, the precipitate was suspended in water or a buffered aqueous solution. A clear, stable colloidal solution was produced.

Variant 5.

A colloidal solution of TiO$_2$ (1.2 g/dm$^3$) in an aqueous solution containing isopropanol (10%) in a nitric acid environment (pH=2.5) was supplemented with crystalline ascorbic acid (KA) at a molar ratio of 1:1 (KA:TiO$_2$), and a red colouration appeared. Next, the resulting sol was brought to pH=7, placed in a dialysis tube and dialysed twice against an aqueous solution of ascorbic acid (5 mmol/dm$^3$, pH=7). An orange, clear colloidal solution was formed, which was used in subsequent experiments. TiO$_2$ nanocrystals modified with ascorbic acid (KA@TiO$_2$) were stable (did not aggregate) at pH=7.

TiO$_2$ nanocrystals modified with ascorbic acid or another organic compound according to the present invention may then be subjected to further modifications consisting of conjugation with a molecule increasing the specificity of their activity (i.e. an antibody, peptide, biotin or vitamins).

EXAMPLE 2

Characteristics of the Produced Materials

Among the materials synthesized according to Example 1, nanocrystals of TiO$_2$ modified with modifier K-1 (K-1@TiO$_2$), rutin (rutin@TiO$_2$) and ascorbic acid (KA@TiO$_2$) were stable at pH=7. The other materials underwent aggregation which was evidenced by the formation of a precipitate at pH >3-4.

Figure 2:
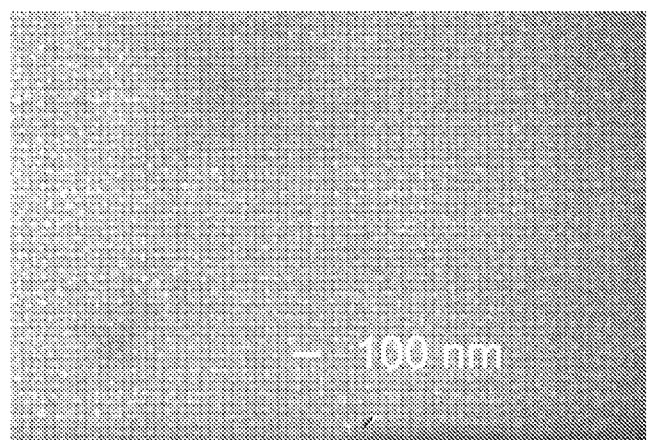
FIG. 2 shows a TEM image recorded for the material K-1@$TiO_2$.

The UV-vis spectrum of K-1@TiO$_2$ is shown in FIG. 1a. Like other materials (stable in an acidic environment) it exhibits an improved absorption of visible light to wavelengths of ca. 500-700 nm. The TEM image shown in FIG. 2 confirms the homogeneity of the material. The individual, non-aggregating particles are from several to a dozen or so nanometers in size.

Figure 1B:
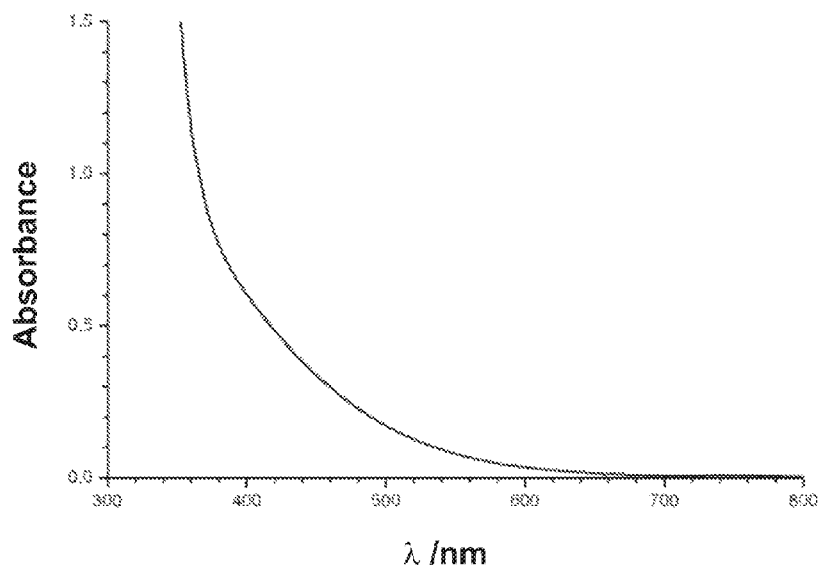

The UV-vis spectrum of KA@TiO$_2$ is shown in FIG. 1b. Like other materials (stable in an acidic environment) KA@TiO$_2$ exhibits an improved absorption of visible light to wavelengths of ca. 600-700 nm.

Figure 1C:
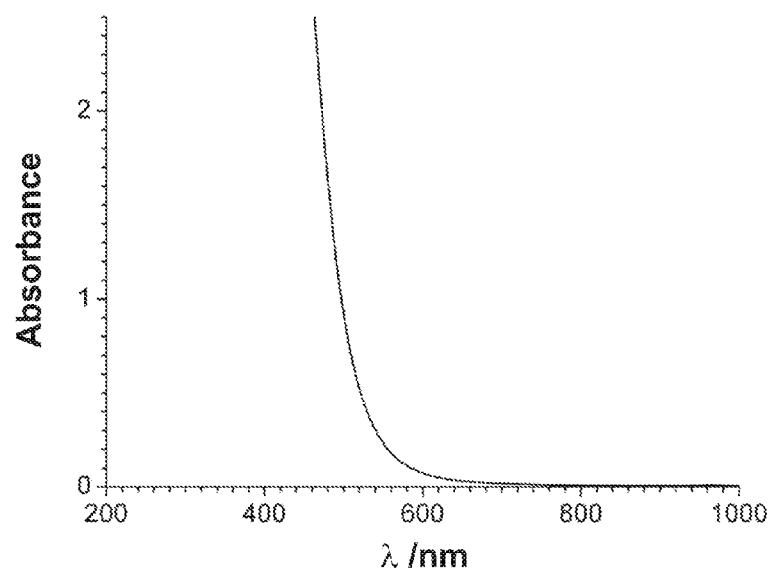

The UV-vis spectrum of rutin@TiO$_2$ is shown FIG. 1c. This material exhibits an improved absorption of visible light to wavelengths of ca. 600 nm.

EXAMPLE 3

Photocatalytic Activity of the Materials and Activity in Photoinactivation of Bacteria Photodegradation assays were performed on bovine albumin (BSA, a model protein) during irradiation with visible light in the presence of nanocrystalline TiO$_2$ modified with an organic compound selected from the group according to the present invention. The concentration of the protein in the solution was assayed semi-quantitatively using electrophoresis in a polyacrylamide gel under denaturing conditions (SDS-PAGE). The reaction mixtures, regardless of the modifications of nanocrystalline TiO$_2$, were prepared using the following method:

A solution of modified TiO$_2$ (in an amount to yield a final concentration of 0.4 mg/ml in terms of TiO$_2$) was mixed with bovine albumin (final concentration 0.4 mg/ml) and water to a final volume of 2 ml.

Irradiation was performed using a high-pressure mercury lamp, HBO-500, as a light source and filters delivering light at a wavelength in the range 420-800 nm. Tests were performed in a quvette purged with a small stream of air during irradiation to ensure a constant oxygen level in solution. During the experiment, samples were taken and subjected to electrophoresis following denaturation in order to monitor the degree of albumin degradation. The electrophoresis was performed in a Laemmli system using a 10% separating gel and a 4% stacking gel. The results are shown in FIG. 3. Sample 0' corresponds to an image of 2 μg of protein.

The photodegradation assays of protein have confirmed the high level of photocatalytic activity of K-1@TiO$_2$ upon visible light irradiation. The compiled protein electrophoresis images show protein degradation over the exposure time in a sample containing the protein and modified titanium dioxide in water. In the spectral range of 400-800 nm (FIG. 3a) one can observe a clear decrease of protein concentration during irradiation. In a narrower radiation ranges, 435-800 nm and 455-800 nm, the results are slightly poorer than the initial ones (FIGS. 3b and 3c).

Protein photodegradation assays have confirmed the high level of photocatalytic activity of KA@TiO$_2$ upon visible light irradiation. During irradiation within the spectral ranges 400-800 nm and 420-800 nm (FIGS. 3d and 3e, respectively) a clear decrease in protein concentration can be observed within several minutes.

Protein photodegradation assays have confirmed the high level of photocatalytic activity of rutin@TiO$_2$ upon visible light irradiation. The compiled protein electrophoresis images show protein degradation over the exposure time in a sample containing the protein and modified titanium dioxide in water. Both in the spectrum range 420-800 nm (FIG. 3f) and in a narrower range of radiation, 455-800 nm (FIG. 3g) one can observe clear decrease in protein concentration throughout the time of exposure.

EXAMPLE 3

Evaluation of the Activity of the Material in the Photoinactivation of Bacteria The assays of the ability of the new materials to photoinactivate microorganisms were performed on a model strain of *Escherichia coli*, and the absence of cytotoxicity in this material to this bacterial strain was demonstrated. The tests assaying the efficiency of the photoinactivation of microorganisms were performed thusly:

A suspension of bacteria in water (ca. $10^6$ CFU/ml determined spectrophotometrically) was supplemented with a colloidal solution of nanocrystalline $TiO_2$ modified with an organic compound selected from the group according to the present invention, to its final concentration of 0.4 mg/ml. The assays were performed under the same irradiation conditions as the protein photodegradation assays (2 ml samples, see above) using a cut-off filter $\lambda > 420$ nm, aerating the sample during irradiation. Small samples were collected in order to evaluate the colony-forming potential of the examined strain. The colony formation ability was determined in dishes through the inoculation of 100 μl aliquots of a serial dilution of the bacterial suspension onto minimal medium (DIFCO) and counting the colonies. The results are shown as cell survival fractions $S/S_0$.

Figure 4:
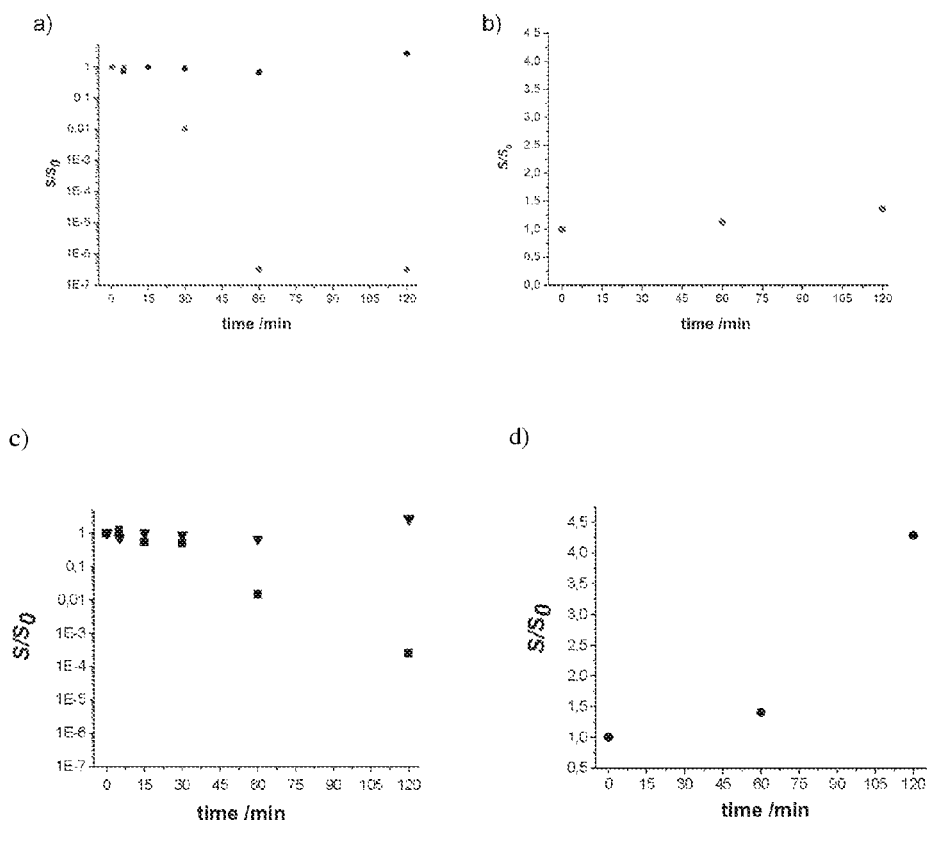
FIG. 4 shows E. coli viability tests in the presence of a colloidal solution of $TiO_2$ nanocrystals modified with K-1 (grey) and lacking the photocatalyst (black) (a) during irradiation with light λ>420 nm and (b) E. coli viability test results in the same system in the dark, as well as E. coli viability tests in the presence of a colloidal solution of $TiO_2$ nanocrystals modified with ascorbic acid (squares) and lacking a photocatalyst (triangles) (c) during irradiation with light λ>420 nm and (d) E. coli viability test results in the same system in the dark.

The results obtained for K-1@$TiO_2$ demonstrate its high activity in the photoinactivation of microorganisms, using the model strain of *E. coli* (FIG. 4a). At the same time, the cytotoxicity of the tested materials was not observed against this strain (FIG. 4b). Analogous results were obtained for KA@$TiO_2$ (photoinactivation—FIG. 4c and cytotoxicity—FIG. 4d).

The invention claimed is:

1. A nanocrystalline photocatalyst active upon visible light irradiation in the form of a transparent colloidal solution, comprising:
   a. a dispersed phase containing nanoparticles of titanium dioxide $TiO_2$ of a size less than 100 nm and surface-modified with an organic compound selected from the group consisting of: disodium salt of 4,5-dihydroxy-1,3-benzenedisulfonic acid, rutin and ascorbic acid, and
   b. a liquid dispersing medium,
wherein the colloidal solution has a pH of about 7.

2. The nanocrystalline photocatalyst of claim 1, wherein the liquid dispersing medium is an aqueous solution.

3. The nanocrystalline photocatalyst of claim 1, wherein the nanoparticles of titanium dioxide are additionally conjugated with a molecule.

4. The nanocrystalline photocatalyst of claim 3, wherein the molecule is an antibody, peptide, biotin, or a vitamin.

5. A nanocrystalline photocatalyst active upon visible light irradiation in the form of a transparent colloidal solution, comprising:
   a. a dispersed phase containing nanoparticles of titanium dioxide $TiO_2$ of a size less than 100 nm and surface-modified with rutin, and
   b. a liquid dispersing medium,
wherein said nanocrystalline photocatalyst exhibits stability in aqueous solutions at pH of about 7.

6. The nanocrystalline photocatalyst of claim 5, wherein the liquid dispersing medium is an aqueous solution.

7. The nanocrystalline photocatalyst of claim 5, wherein the nanoparticles of titanium dioxide are additionally conjugated with a molecule.

8. The nanocrystalline photocatalyst of claim 7, wherein the molecule is an antibody, peptide, biotin, or a vitamin.

9. A method of producing a nanocrystalline photocatalyst active upon visible light irradiation in the form of a transparent colloidal solution, comprising:
   a. supplementing into a colloidal aqueous solution of $TiO_2$ with an organic compound to form a sol, wherein the organic compound undergoes chemisorption on the surface of $TiO_2$ and is selected from the group consisting of: disodium salt of 4,5-dihydroxy-1,3-benzenedisulfonic acid, rutin and ascorbic acid,
   b. bringing the pH of the resulting sol of step a) to about 7 and performing dialysis on the resulting sol against an aqueous solution to form a stable suspension of nanoparticles of titanium dioxide $TiO_2$ of a size less than 100 nm.

10. The method of claim 9, wherein the chemisorption is performed in an acidic environment.

11. The method of claim 10, wherein the chemisorption is performed at pH of about 2.5.

12. The method of claim 10, wherein the chemisorption is performed in the presence of nitric acid.

13. The method of claim 10, wherein after the chemisorption is complete, the resulting colloidal solution is brought to pH of about 7 using an aqueous solution of a base.

14. The method of claim 9, wherein the chemisorption is performed in the presence of an alcohol.

15. The method of claim 14, wherein the alcohol is isopropanol.

16. The method of claim 9, wherein a colloidal solution of $TiO_2$ is supplemented with the organic compound at a molar ratio of 1:1.

17. A method of producing a layer on a solid substrate, comprising coating the solid substrate with the nanocrystalline photocatalyst of claim 1.

18. The method of claim 17, wherein the solid substrate is glass, metal, plastics or paper.

19. A preparation comprising:
   the nanocrystalline photocatalyst of claim 1.

20. The preparation of claim 19, wherein the preparation is a photosterilizing, photobacteriocidal, photomycocidal, or photocatalytic preparation.

21. A method, comprising:
   applying the preparation of claim 10 on surfaces of glass and plastic elements.

22. The method of claim 21, wherein the preparation is applied on a contact lens, a medical catheter, or a glass or plastic conduit.

* * * * *

UNITED STATES PATENT AND TRADEMARK OFFICE
CERTIFICATE OF CORRECTION

PATENT NO.        : 9,040,489 B2
APPLICATION NO.   : 13/148192
DATED             : May 26, 2015
INVENTOR(S)       : Przemyslaw Labuz et al.

It is certified that error appears in the above-identified patent and that said Letters Patent is hereby corrected as shown below:

In the claims

In column 12, line 46 (approx.), in Claim 21, delete "claim 10" and insert -- claim 19 --

Signed and Sealed this
First Day of December, 2015

Michelle K. Lee
*Director of the United States Patent and Trademark Office*